(12) United States Patent
Shen

(10) Patent No.: US 9,903,499 B2
(45) Date of Patent: Feb. 27, 2018

(54) PROPORTIONAL VALVE

(71) Applicant: BEIJING AEONMED CO., LTD., Beijing (CN)

(72) Inventor: Youfang Shen, Beijing (CN)

(73) Assignee: BEIJING AEONMED CO., LTD., Beijing (CN)

( * ) Notice: Subject to any disclaimer, the term of this patent is extended or adjusted under 35 U.S.C. 154(b) by 15 days.

(21) Appl. No.: 14/894,903

(22) PCT Filed: May 28, 2014

(86) PCT No.: PCT/CN2014/078647
§ 371 (c)(1),
(2) Date: Nov. 30, 2015

(87) PCT Pub. No.: WO2014/190904
PCT Pub. Date: Dec. 4, 2014

(65) Prior Publication Data
US 2016/0116078 A1    Apr. 28, 2016

(30) Foreign Application Priority Data
May 31, 2013 (CN) .......................... 2013 1 0215594

(51) Int. Cl.
*F16K 31/06* (2006.01)
*A61M 16/20* (2006.01)
(Continued)

(52) U.S. Cl.
CPC ....... *F16K 31/0655* (2013.01); *A61M 16/202* (2014.02); *A61M 16/203* (2014.02);
(Continued)

(58) Field of Classification Search
CPC . F16K 31/0655; F16K 41/12; G05D 16/2013; A61M 16/202; A61M 16/203; A61M 16/205
(Continued)

(56) References Cited

U.S. PATENT DOCUMENTS 3,606,241 A * 9/1971 Bornholdt ........... F16K 31/0693
251/129.07
5,927,275 A * 7/1999 Loser .................. A61M 16/205
128/204.21
(Continued)

FOREIGN PATENT DOCUMENTS

CN    201180834 Y    1/2009
CN    101482193 A    7/2009
(Continued)

OTHER PUBLICATIONS

International Search Report (with English translation), International Application No. PCT/CN2014/078647, mailed Aug. 22, 2014.

*Primary Examiner* — Ian Paquette
(74) *Attorney, Agent, or Firm* — Marshall, Gerstein & Borun LLP

(57) ABSTRACT

The proportional valve including a valve body, an air inlet hole and an air outlet hole being provided inside the valve body; a valve core component, the valve core component being movably disposed inside the valve body along a vertical direction; and a first film sheet, an outer side of the first film sheet being connected to the valve body, and an inner side of the film sheet being connected to the valve core component. The proportional valve has a high response speed, high precision, desirable repeatability, desirable consistency, small hysteresis, low fabrication difficulty, and low fabrication cost.

8 Claims, 2 Drawing Sheets

(51) Int. Cl.
    *F16K 41/12*     (2006.01)
    *G05D 16/20*     (2006.01)

(52) U.S. Cl.
    CPC ........... *A61M 16/205* (2014.02); *F16K 41/12* (2013.01); *G05D 16/2013* (2013.01)

(58) Field of Classification Search
    USPC .................................................... 251/129.17
    See application file for complete search history.

(56) References Cited

U.S. PATENT DOCUMENTS

| | | | |
|---|---|---|---|
| 6,581,904 B2 | 6/2003 | Watanabe et al. | |
| 6,719,268 B2 * | 4/2004 | Fukano | F16K 7/14 251/129.17 |
| 6,910,674 B2 * | 6/2005 | Niemela | A61M 16/20 251/129.17 |
| 9,133,955 B2 | 9/2015 | Shen | |
| 2004/0007232 A1 * | 1/2004 | Rochat | A61M 16/205 128/205.24 |

FOREIGN PATENT DOCUMENTS

| | | |
|---|---|---|
| CN | 201672112 U | 12/2010 |
| CN | 103185163 A | 7/2013 |
| CN | 203322314 U | 12/2013 |
| EP | 0968024 A1 | 1/2000 |
| JP | H0821558 A | 1/1996 |
| JP | H09229231 | 9/1997 |

* cited by examiner

PROPORTIONAL VALVE

This patent application claims the priority of the Chinese Patent Application No. 201310215594.3, entitled Proportional Valve, filed on May 31, 2013, by Beijing Aeonmed Co. Ltd, the disclosure of which is incorporated herein by reference in its entirety.

TECHNICAL FIELD OF THE INVENTION

The invention relates to the medical field, especially relates to a proportional valve.

BACKGROUND

At present, the existing proportional valve has the disadvantage of a low response speed.

SUMMARY OF THE INVENTION

The purpose of this invention is to at least solve one of the above technical problems to some extent or at least provide a useful commercial option. Therefore, one object of the invention is to provide a proportional valve.

For realizing the object, according to an embodiment of the invention, the invention provides a proportional valve. The proportional valve comprises a valve body, an air inlet pore and an air outlet pore being provided within the valve body; a valve core component, the valve core component being set movably inside the valve body along an up-down direction; and a first diaphragm, the outside of the first diaphragm connecting to the valve body and the inside of the first diaphragm connecting to the valve core component.

By setting the first diaphragm, the inner side of which connects to the valve core component and the outer side of which connects to the valve body, in the proportional valve according to the embodiment of the invention (namely the valve core component is supported on the valve body by the first diaphragm), the valve core component is separated from the valve body. Due to this separation, the valve core component moves along the up-down direction inside the valve body and is out of touch with the valve body, namely there is no friction between the valve core component and the valve body when the valve core component moves along the up-down direction inside the valve body. It is beneficial to improve the response speed, precision, repeatability and consistency of the proportional valve, and also reduce the hysteresis of the proportional valve.

Furthermore, the proportional valve according to the above embodiment of the invention may also have the following additional technical features:

According to one embodiment of the invention, the proportional valve includes: a body, the body including the air inlet pore and the air outlet pore; a diaphragm seat, the diaphragm seat being installed on the body and the outer side of the first diaphragm connecting to the diaphragm seat; an upper magnetic seat, the upper magnetic seat being installed on the diaphragm seat; a magnet ring, the magnet ring being installed on the upper magnetic seat; and a magnetic core, the magnetic core being installed on the magnet ring and a part of the magnetic core being located internal of the magnet ring. It is not only beneficial to form magnetic field, but also enables the first diaphragm to connect more stably to the valve body by installing the diaphragm seat, further to improve the stability of the valve core component.

According to one embodiment of the invention, the valve core component includes: a valve coverplate, the valve coverplate being installed inside the air outlet pore and being opposed to the air inlet pore; a kicker pin, the kicker pin connecting to the valve coverplate and then extending through the diaphragm seat, the inner side of the first diaphragm connecting to the kicker pin; and a coil, the coil connecting to the kicker pin and one part of the coil being located inside the magnet ring, a part of the magnetic core being located inside the coil. Therefore, the valve core component has the advantages of a simple structure etc.

According to one embodiment of the invention, the diaphragm seat comprises an upper diaphragm seat and a lower diaphragm seat being installed on the upper diaphragm seat, the upper diaphragm seat is installed on the body, the outer side of the first diaphragm is clamped between the upper diaphragm seat and the lower diaphragm seat in order to set the valve coverplate expediently.

According to one embodiment of the invention, a seal ring is installed between the upper diaphragm seat and the body in order to protect the gas from leaking between the upper diaphragm seat and the body.

According to one embodiment of the invention, the kicker pin extends through the coil and the magnetic core, and the valve core component also includes a second diaphragm, the outer side of the second diaphragm connecting to the magnetic core and the inner side of the second diaphragm connecting to the part of the kicker pin extending through the magnetic core. Thereby, it is possible to make the valve core component more stable in the procedure of the up-down motion such that it ensures higher precision, better repeatability of the proportional valve.

According to one embodiment of the invention, the valve body also comprises a diaphragm support plate, the diaphragm support plate is installed on the magnetic core, and the outer side of the second diaphragm is clamped between the magnetic core and the diaphragm support plate. Therefore, the second diaphragm connects to the valve body more expediently and more stably in order to enhance the stability of the valve core component moving along an up-down direction and further improve the precision and repeatability of the proportional valve.

According to one embodiment of the invention, the upper magnet seat includes a first connection terminal and a second connection terminal. One end of the coil conductor connects to the first connection terminal and another end of the coil conductor connects to the second connection terminal. Thereby, it is possible to electrify the coil conductor more easily and more conveniently.

According to one embodiment of the invention, the valve body also includes a spacer bush, the spacer bush being installed on the upper surface of the magnetic core. The outer periphery surface of the spacer bush touches the internal periphery surface of the magnet ring. Thereby, it is possible to ensure the coaxiality of the magnetic core and the magnet ring.

The invention will present the additional aspects and advantages in the following description, and the partial additional aspects and advantages could become obvious in the following description or via the practice of the invention.

BRIEF DESCRIPTION OF DRAWINGS

The above and/or additional aspects and advantages of the invention will become obvious and easy to understand from the description of embodiments with reference to the following drawings, wherein.

DETAILED DESCRIPTION OF THE EMBODIMENTS

Figure 1:
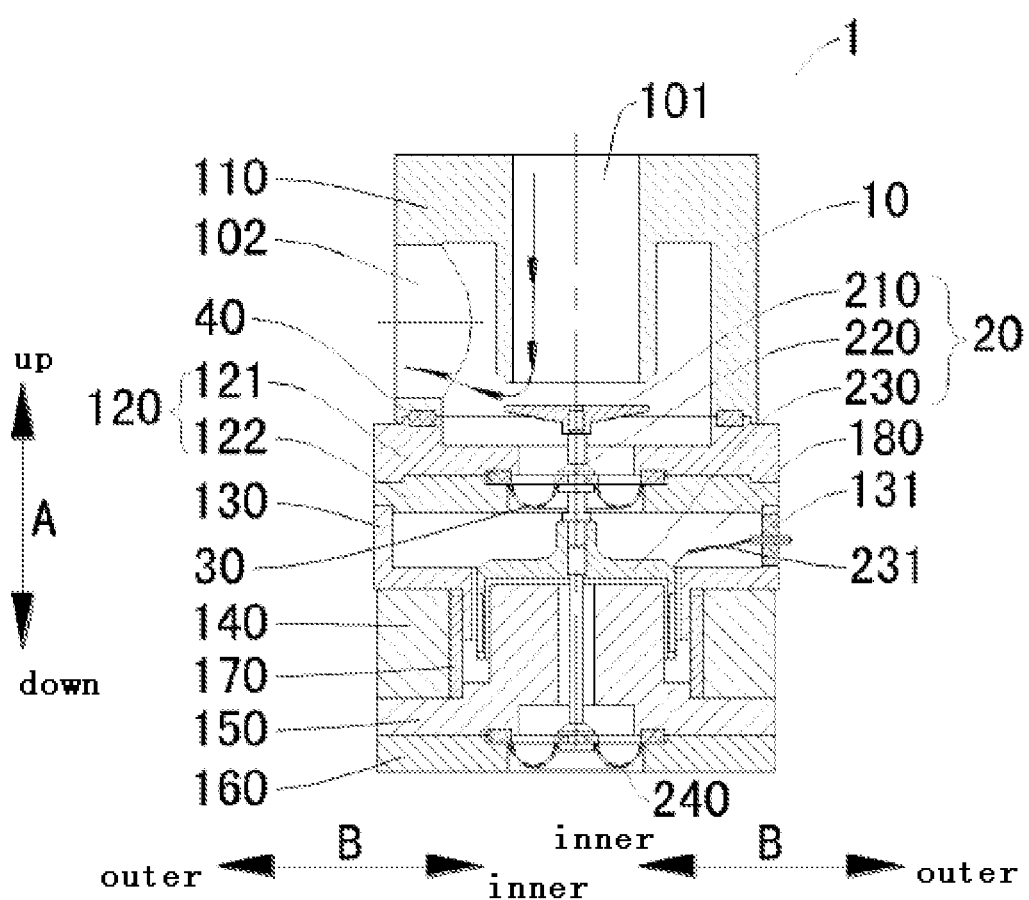
FIG. 1 is a diagram illustrating the structure of a proportional valve in the invention.

Hereinafter, embodiments of the invention are described in detail, examples of which are shown in the drawings, wherein the same or similar labels represent the same or similar components or the components of the same or similar function. The following embodiments described with reference to the drawings are exemplary, which are aimed at explaining the invention rather than restricting the invention, In the description of the invention, the technical words are "center", "lengthways", "widthways", "length", "width", "thickness", "upper", "lower", "front", "back", "left", "right", "up-down", "horizontal", "top", "bottom", "inner", "outer", "clockwise", "anticlockwise" et al. these words represent orientation or position relationship shown based on the drawings in order to describe the invention and simplify the description and not to indicate or imply that the indicated device or component must have a specific orientation or constructed and operated in a specific orientation. Therefore, it is not to be understood as a restriction for the invention.

Also the technical words "first", "second" are only be used for a descriptive purpose, and are not to be understood to indicate or imply the relative importance or imply the number of the indicated technical features. Therefore, features defined with "first", "second" may include one or more of the features explicitly or implicitly. In the description of the invention, "multiple" means two or more than two, unless specifically defined otherwise.

In the invention, the technical words "install", "be linked to", "connect to", "fix" et al. should be understood in generalization, unless specifically defined otherwise. For example, these technical words are described as fixed joint or removable connection or the integration of the connection; or mechanical joint or electrical connection; or direct connection or indirect connection via the middle medium or internal connection between the two components. The skilled persons in the art can understand the specific meaning about these technical words in the invention according to the specific circumstance.

In the invention, unless specifically defined otherwise, the first feature being located on the second feature or under the second feature could disclose the direct connection between the first feature and the second feature, and could also disclose that the first feature is not directly connected to the second feature but adopts other ways to connect to the second feature. Furthermore, the first feature being located "above" and "on" the second feature means that the first feature is located right above the second feature or above the second feature, or only means that the horizontal height of the first feature is higher than that of the second feature. Also the first feature being located "under" and "below" the second feature means that the first feature is located right under the second feature or under the second feature, or only means that the horizontal height of the first feature is lower than that of the second feature.

Hereinafter, a proportional valve 1 according to the embodiment of the invention will be described with reference to FIG. 1 and FIG. 2. According to the description of the FIG. 1 and the FIG. 2, the proportional valve 1 according to the embodiment of the invention includes a valve body 10, a valve core component 20 and a first diaphragm 30.

The valve body 10 has an air inlet pore 101 and an air outlet pore 102. The valve core component 20 is installed inside the valve body 10 movably along an up-down direction. The outer side of the first diaphragm 30 connects to the valve body 10 and the inner side of the first diaphragm 30 connects to the valve core component 20. The up-down direction is as shown by an arrow A in the FIG. 1 and the FIG. 2. The inside-outside direction is as shown by an arrow B in the FIG. 1 and the FIG. 2.

During the working time process of the proportional valve 1, according to the movement of the valve core component 20 along a vertical direction, the distance between the valve core component 20 and the air inlet pore 101 may be adjusted in order to change the gas flow crossing through the proportional valve 1. In other words, the gases cross through the air inlet pore 101 and then enter into the proportional valve 1, and then enter into the air outlet pore 102 from the gap between the valve core component 20 and the air inlet pore 101. The size of the gap between the valve core component 20 and the air inlet pore 101 could change with the movement of the valve core component 20 along an up-down direction inside the valve body 10 (specifically, the valve core component 20 moves upward to reduce the gap; the valve core component 20 moves downward to increase the gap). The aim to do so is to control the gas flow.

By setting the first diaphragm 30, the inner side of which connects to the valve core component 20 and the outer side of which connects to the valve body 10, in the proportional valve 1 according to the embodiment of the invention (namely the valve core component 20 is supported on the valve body 10), the valve core component 20 is separated from the valve body 10. Due to this separation, the valve core component 20 moves along the up-down direction inside the valve body 10 and is out of touch with the valve body 10, namely there is no friction between the valve core component 20 and the valve body 10, when the valve core component 20 moves along the up-down direction inside the valve body 10. It is beneficial to improve the response speed, the precision, repeatability and consistency of the proportional valve and also reduce the hysteresis of the proportional valve 1.

Furthermore, since there is no friction between the valve core component 20 and the valve body 10, there is no requirement on the material and the fabrication precision of the valve core component 20 and the valve body 10, in order to reduce the manufacturing difficulty and cost of the proportional valve 1. Therefore, the proportional valve 1 according to the embodiment of the invention has advantages of fast response speed, high precision, good repeatability, good consistency, low hysteresis, low manufacturing difficulty and low manufacturing cost, etc.

In the state shown in the FIG. 1, the valve core component 20 is separated from the air inlet pore 101, the gases enter into the air outlet pore 102 by means of the gap between the valve core component 20 and the air inlet pore 101. In the state shown in the FIG. 2, the valve core component 20 covers the air inlet pore 101, at this time the gas cannot enter into the air outlet pore 102 from the air inlet pore 101. Therefore, the gas cannot cross through the proportional valve 1.

Figure 2:
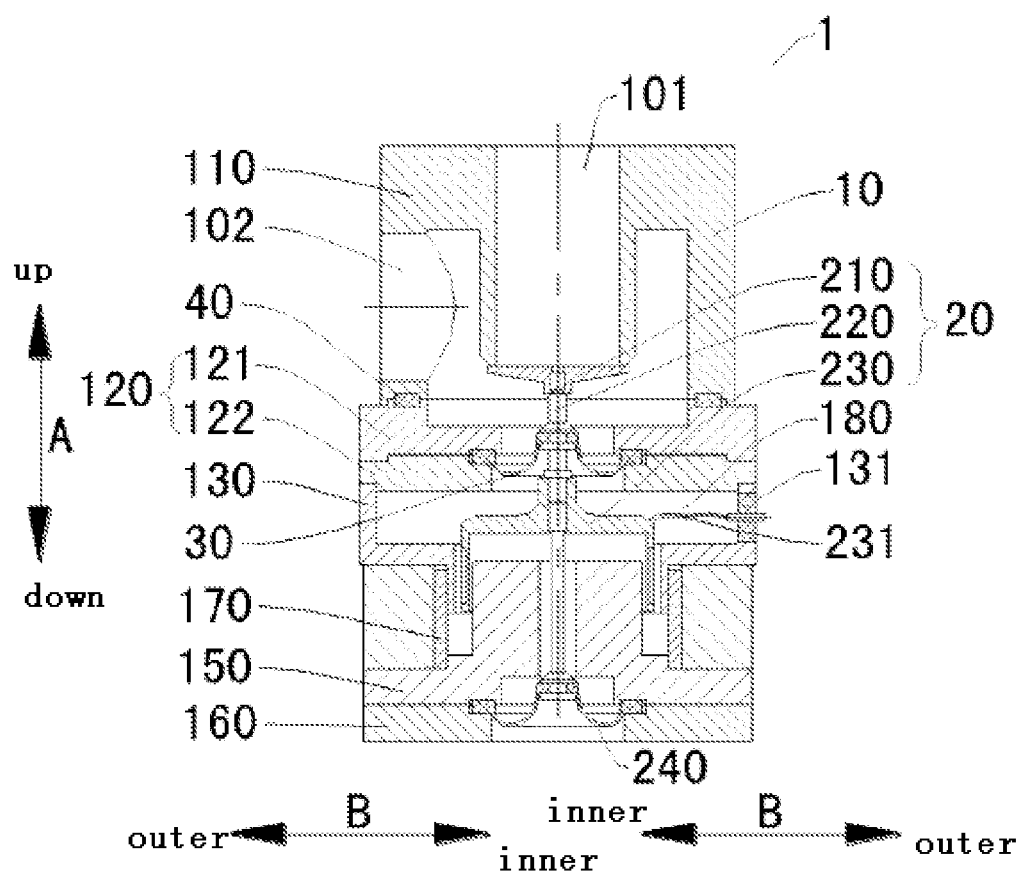
FIG. 2 is a diagram illustrating the structure of a proportional valve in the invention.

As shown in the FIG. 1 and FIG. 2, in some embodiments of the invention, the valve body 10 includes a body 110, a diaphragm seat 120, an upper magnet seat 130, a magnet ring 140 and a magnetic core 150. The body 110 has the air inlet pore 101 and the air outlet pore 102. The diaphragm seat 120 is installed on the body 110; the outer side of the first diaphragm 30 connects to the diaphragm seat 120; the upper magnet seat 130 is installed on the diaphragm seat 120; the magnet ring 140 is installed on the upper magnet seat 130; the magnetic core 150 is installed on the magnet ring 140; a part of the magnetic core 150 is located inside the magnet ring 140. It is beneficial to form magnetic field. By installing the diaphragm seat 120, the first diaphragm 30 could more stably connect to the valve body 10 in order to improve the stability of the valve core component 20.

In one embodiment of the invention, as shown in the FIG. 1 and FIG. 2, the valve core component 20 comprises a valve coverplate 210, a kicker pin 220 and a coil 230. The valve coverplate 210 is installed inside the air outlet pore 102 and is oppose to the air inlet pore 101. The kicker pin 220 connects to the valve coverplate 210 and crosses through the diaphragm seat 120, and the kicker pin 220 connects to the inner side of the first diaphragm 30. The coil 230 connects to the kicker pin 220 and a part of the coil 230 is located inside the magnet ring 140, and a part of the magnetic core 150 is located inside the coil 230. Therefore, the valve core component 20 has the advantages of the simple structure, etc.

When adjusting the gas flow which crosses through the proportional valve 1, the amplitude of the electric current flowing into the coil 230 may be changed (for example, exerting impulse voltage on the coil 230) so as to change the magnetism of the coil 230 in order to change the acting force between the coil 230 and the magnetic core 150. Specifically, increasing the current which flows into the coil 230 could give a rise to the magnetism of the coil 230 and further give a rise to the acting force between the coil 230 and the magnet core 150. The coil 230 correspondingly moves upward in order to reduce the gap between the valve coverplate 210 and the air inlet pore 101, and decrease the gas flow crossing through the proportional valve 1. Oppositely, decreasing the electric current value which flows into the coil 230 may increase the gas flow crossing through the proportional valve 1.

As shown in the FIG. 1 and FIG. 2, advantageously, the diaphragm seat 120 includes an upper diaphragm seat 121 and a lower diaphragm seat 122 being located on the upper diaphragm seat 121. The upper diaphragm seat 121 is installed on the body 110. The outer side of the first diaphragm 30 is located between the upper diaphragm seat 121 and the lower diaphragm seat 122 in order to set the valve coverplate 210. Specifically, the kicker pin 220 crosses through the upper diaphragm seat 121 and the lower diaphragm seat 122 along the up-down direction.

The horizontal sections of each of the upper diaphragm seat 121 and the lower diaphragm seat 122 are both the circular shape. The upper diaphragm seat 121 is installed on the lower surface of the body, and the lower diaphragm seat 122 is installed on the lower surface of the upper diaphragm seat 121. Advantageously, as shown in the FIG. 1 and FIG. 2, a seal ring 40 is installed between the upper diaphragm seat 121 and the body 110 in order to protect the gas from leaking from between the upper diaphragm seat 121 and the body 110.

As shown in the FIG. 1 and FIG. 2, in some embodiments of the invention, the kicker pin 220 crosses through the coil 230 and the magnetic core 150, and the valve core component 20 also comprises a second diaphragm 240. The outer side of the second diaphragm 240 connects to the magnetic core 150 and the inner side of the second diaphragm 240 connects to the part of the kicker pin 220 crossing through the magnetic core 150. In other words, both the first diaphragm 30 and the second diaphragm 240 support the valve core component 20 in order to improve the stability of the valve core component 20 during the movement along the up-down direction, and achieve higher precision and the better repeatability of the proportional valve 1.

Specifically, as shown in the FIG. 1 and FIG. 2, the valve body 10 also includes a diaphragm support plate 160, the diaphragm support plate 160 being installed on the magnetic core 150. Since the outer side of the second diaphragm 240 may be clamped between the magnetic core 150 and the diaphragm support plate 160, the second diaphragm 240 connects to the valve body 10 more conveniently and more stably in order to improve the stability of the valve core component 20 during the movement along the up-down direction, such that the proportional valve 1 achieves higher precision and the better repeatability. The diaphragm support plate 160 is installed on the lower surface of the magnetic core 150 and the horizontal section of the diaphragm support plate 160 is the circular shape.

As shown in the FIG. 1 and FIG. 2, in an example of the invention, the valve body 10 also includes a spacer bush 170, the spacer bush 170 being installed on the upper surface of the magnetic core 150 and the outer peripheral surface of the spacer bush 170 has touched on the inner peripheral surface of the magnet ring 140. Because of installing the spacer bush 170, it is possible to ensure the coaxiality of the magnetic core 150 and the magnet ring 140.

Specifically, as shown in the FIG. 1 and FIG. 2, the upper magnet seat 130 is installed on the lower surface of the lower diaphragm seat 122, the horizontal section of the upper magnet seat 130 is the circular shape. The upper magnet seat 130 includes a first vertical unit, a horizontal unit and a second vertical unit. The first vertical unit is installed on the lower surface of the lower diaphragm seat 122 and the horizontal unit is installed on the upper surface of the magnet ring 140. The outer edge of the horizontal unit connects to the lower edge of the first vertical unit and the inner edge of the horizontal unit connects to the upper edge of the second vertical unit. The inner peripheral surface of the spacer bush 170 has touched the outer peripheral surface of the second vertical unit, namely the spacer bush 170 is clamped between the magnet ring 140 and the second vertical unit. An accommodation space 180 is defined between the upper magnet seat 130 and the spacer bush 170 and the coil 230 is located inside the accommodation space 180. The spacer bush 170 is installed on the upper surface of the magnet core 150.

The magnet ring 140 is cylindrical shape, and its horizontal section is circular shape. The magnet ring 140 is installed on the lower surface of the upper magnet seat 130. The horizontal section of the magnetic core 150 is circular shape and the magnet ring 140 is installed on the upper surface of the magnetic core 150 and a part of the magnetic core 150 is located inside the accommodation space 180. A part of the coil 230 is located between the second vertical unit and the magnetic core 150.

As shown in the FIG. 1 and FIG. 2, in a specific example of the invention, the upper magnet seat 130 includes a first connection terminal 131 and a second connection terminal. One end of the conductor 231 of the coil 230 connects to the first connection terminal 131 and the other end of the conductor 231 connects to the second connection terminal. Thereby, it is possible to electrify the conductor 231 of the coil 230 more easily and more conveniently.

In the description of the specification, references to the technical words "an embodiment", "some embodiments", "an example", "a specific example" or "some examples" et al. mean that specific features, structures, materials described in combination with the embodiment or example are embodied in at least one embodiment or example of the invention. In the specification, the schematic expressions of these technical words do not necessarily refer to the same embodiment or example. Furthermore, the described specific features, structures, materials or characteristics may be combined within any of one or more embodiments or examples in a suitable manner.

Although embodiments of the invention have been illustrated and described in the above, it is to be understood that the above mentioned embodiments are exemplary rather than the limitation of the invention. Those skilled in the art may make alterations, substitution and modifications to the above mentioned embodiments within the scope of the invention and without departing from the principle and gist of the invention.

The invention claimed is:

1. A proportional valve, comprising:
    a valve body, the valve body having an air inlet pore and an air outlet pore;
    a valve core component, the valve core component being installed inside the valve body movably along an up-down direction; and
    a first diaphragm, an outer side of the first diaphragm connecting to the valve body and an inner side of the first diaphragm connecting to the valve core component; and
    a kicker pin crossing through a coil and a magnetic core;
    wherein the valve core component includes a second diaphragm, an outer side of the second diaphragm connecting to the magnetic core, and an inner side of the second diaphragm connecting to a part of the kicker pin extending through the magnetic core.

2. The proportional valve according to claim 1, wherein the valve body also includes a diaphragm support plate, the diaphragm support plate being installed on the magnetic core, and the outer side of the second diaphragm being clamped between the magnetic core and the diaphragm support plate.

3. The proportional valve according to claim 1, wherein the valve body includes:
    a body, the body having the air inlet pore and the air outlet pore;
    a diaphragm seat, the diaphragm seat being installed on the body and the outer side of the first diaphragm connecting to the diaphragm seat;
    an upper magnet seat, the upper magnet seat being installed on the diaphragm seat; and
    a magnet ring, the magnet ring being installed on the upper magnet seat;
    wherein the magnetic core is installed on the magnet ring and a part of the magnetic core is located inside the magnet ring.

4. The proportional valve according to claim 3, wherein the diaphragm seat includes an upper diaphragm seat and a lower diaphragm seat being installed on the upper diaphragm seat, and the upper diaphragm seat is installed on the body, and the outer side of the first diaphragm is clamped between the upper diaphragm seat and the lower diaphragm seat.

5. The proportional valve according to claim 4, wherein a seal ring is installed between the upper diaphragm seat and the body.

6. The proportional valve according to claim 3, wherein the valve core component includes:
    a valve coverplate, the valve coverplate being installed inside the air outlet pore and opposing to the air inlet pore;
    wherein the kicker pin connects to the valve coverplate and crosses through the diaphragm seat, and the inner side of the first diaphragm connects to the kicker pin; and
    wherein the coil connects to the kicker and a part of the coil is located inside the magnet ring, and a part of the magnetic core is located inside the coil.

7. The proportional valve according to claim 6, wherein the upper magnet seat includes a first connection terminal and a second connection terminal, and one end of a coil conductor connecting to the first connection terminal, and the other end of the conductor connecting to the second connection terminal.

8. The proportional valve according to claim 6, wherein the valve body also includes a spacer bush, the spacer bush being installed on the upper surface of the magnetic core, and the outer peripheral surface of the spacer bush touching on the inner peripheral surface of the magnet ring.

* * * * *

UNITED STATES PATENT AND TRADEMARK OFFICE
CERTIFICATE OF CORRECTION

PATENT NO. : 9,903,499 B2  
APPLICATION NO. : 14/894903  
DATED : February 27, 2018  
INVENTOR(S) : Youfang Shen Page 1 of 1

It is certified that error appears in the above-identified patent and that said Letters Patent is hereby corrected as shown below:

On the Title Page

At item (57), Line 1, "The proportional" should be -- A proportional --.

In the Claims

At Column 8, Line 29, "kicker and" should be -- kicker pin, and --.

Signed and Sealed this  
Second Day of April, 2019

Andrei Iancu  
*Director of the United States Patent and Trademark Office*